United States Patent
Kothari et al.

(10) Patent No.: US 10,866,835 B2
(45) Date of Patent: Dec. 15, 2020

(54) DATA USAGE EFFECTIVENESS DETERMINATION

(71) Applicant: Hewlett-Packard Development Company, L.P., Houston, TX (US)

(72) Inventors: Sunil Kothari, Palo Alto, CA (US); Michael L. Reasoner, Corvallis, OR (US); Thomas J Peck, Corvallis, OR (US); Douglas A Sexton, San Diego, CA (US); Francisco Oblea, Tlaquepaque (MX); Jun Zeng, Palo Alto, CA (US); Gary J Dispoto, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 189 days.

(21) Appl. No.: 15/764,326

(22) PCT Filed: Nov. 23, 2015

(86) PCT No.: PCT/US2015/062116
§ 371 (c)(1),
(2) Date: Mar. 29, 2018

(87) PCT Pub. No.: WO2017/091195
PCT Pub. Date: Jun. 1, 2017

(65) Prior Publication Data
US 2019/0050259 A1  Feb. 14, 2019

(51) Int. Cl.
*G06F 9/46* (2006.01)
*G06F 9/50* (2006.01)
(Continued)

(52) U.S. Cl.
CPC .......... *G06F 9/5011* (2013.01); *G06Q 10/06* (2013.01); *G16H 50/50* (2018.01)

(58) Field of Classification Search
None
See application file for complete search history.

(56) References Cited

U.S. PATENT DOCUMENTS 6,463,346 B1  10/2002 Flockhart et al.
6,618,168 B1  9/2003 Nakajima et al.
(Continued)

FOREIGN PATENT DOCUMENTS

DE  102013102756 A1  9/2014
JP    2009265699 A   11/2009
(Continued)

OTHER PUBLICATIONS

Real-time and Data-driven Operation Optimization and Knowledge Discovery for an Enterprise Information System, 2014.

*Primary Examiner* — Kenneth Tang
(74) *Attorney, Agent, or Firm* — Tong Rea Bentley & Kim LLC

(57) ABSTRACT

Examples disclosed herein relate to determining data usage effectiveness. A processor may determine data usage effectiveness information related to an entity's workflow based on workflow data collected related to the entity's operations and metrics determined based on the data. The determination may be based on a comparison of the information related to the entity's workflow to target workflow information and priority information associated with the target workflow information. The processor may output information related to the determined data usage effectiveness.

15 Claims, 6 Drawing Sheets

(51) Int. Cl.
*G06Q 10/06* (2012.01)
*G16H 50/50* (2018.01)

(56) References Cited

U.S. PATENT DOCUMENTS

| | | | |
|---|---|---|---|
| 7,065,493 B1* | 6/2006 | Homsi | G06Q 10/06 705/7.26 |
| 7,265,860 B2 | 9/2007 | Ferlitsch et al. | |
| 7,454,263 B2 | 11/2008 | Hauck | |
| 7,626,717 B2 | 12/2009 | Rai et al. | |
| 2005/0197821 A1* | 9/2005 | Choi | G06Q 10/06 703/22 |
| 2007/0094060 A1* | 4/2007 | Apps | G06Q 10/00 705/7.36 |
| 2010/0049740 A1* | 2/2010 | Iwase | G06F 19/321 705/7.27 |
| 2012/0016713 A1 | 1/2012 | Wilcock et al. | |
| 2012/0078678 A1* | 3/2012 | Pradhan | G06Q 10/06 705/7.27 |
| 2013/0226639 A1* | 8/2013 | Yokoyama | G06Q 10/06 705/7.14 |
| 2014/0114673 A1* | 4/2014 | Hu | G06F 19/325 705/2 |
| 2014/0129285 A1 | 5/2014 | Wu et al. | |
| 2014/0278717 A1* | 9/2014 | Hinckley | G06Q 10/06316 705/7.26 |
| 2015/0312422 A1* | 10/2015 | Leemet | H04L 41/082 455/406 |
| 2017/0124263 A1* | 5/2017 | Crafts, Jr. | G16H 40/20 |

FOREIGN PATENT DOCUMENTS

| | | |
|---|---|---|
| JP | 2014-191603 A | 10/2014 |
| WO | WO-2014-084829 A1 | 6/2014 |

* cited by examiner

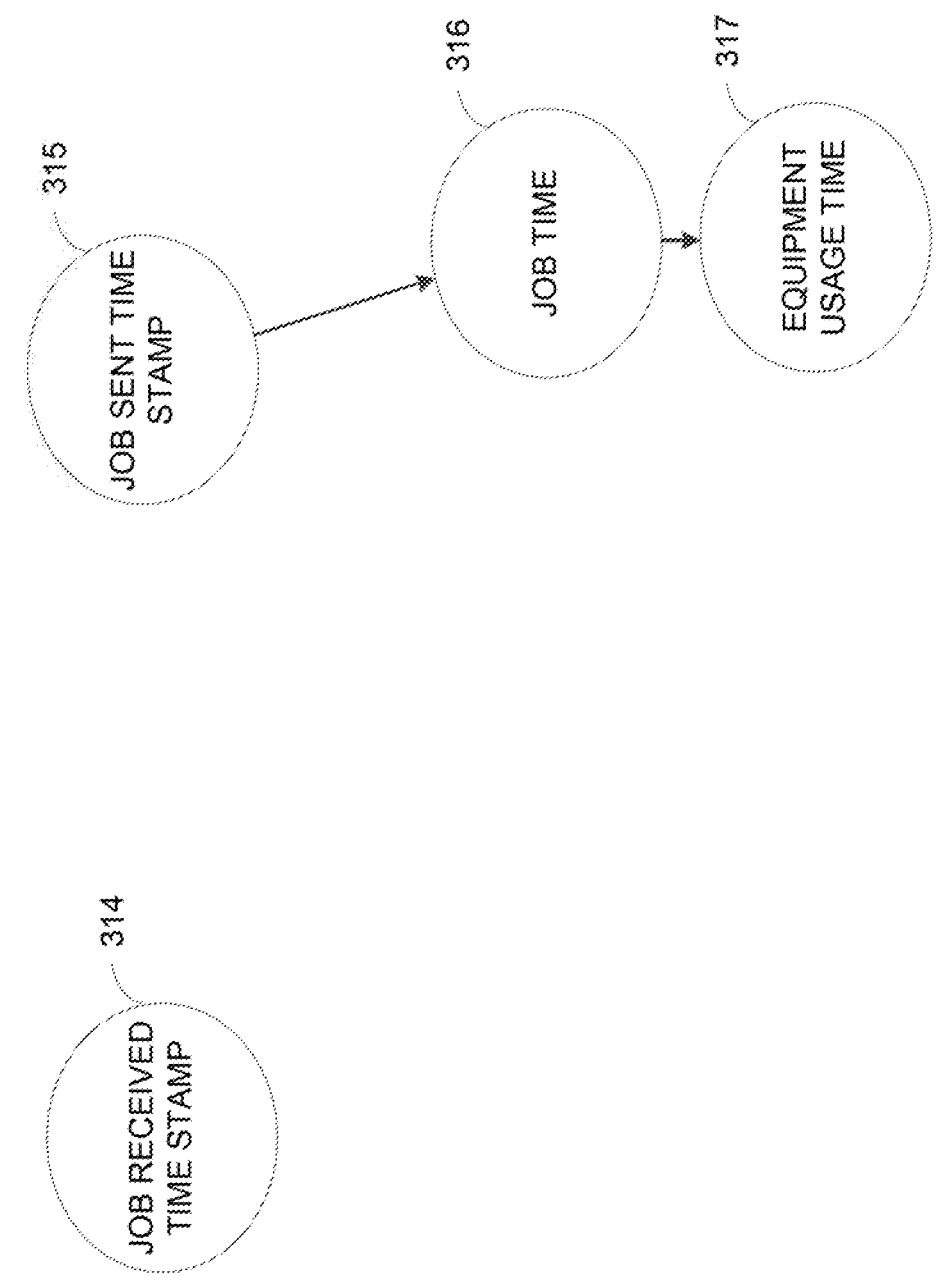

DATA USAGE EFFECTIVENESS DETERMINATION

BACKGROUND

A workflow process may be followed, for example, by a transportation, additive manufacturing, or health care entity. The workflow process may involve multiple sites, pieces of equipment, and workers. In one implementation, the workflow is managed by a software application. For example, the software application may schedule production or assign equipment in a manufacturing environment.

BRIEF DESCRIPTION OF THE DRAWINGS

The drawings describe example embodiments. The following detailed description references the drawings, wherein:

FIGS. 3A-3D are diagrams illustrating examples of determining data usage effectiveness.

DETAILED DESCRIPTION

Entities use increasing amounts of data and increasingly complex workflow processes. The degree and manner to which an entity uses the data effectively may vary by entity, and in some cases, the entity may be unaware of how it is using data related to its workflow and how to make meaningful improvements. In one implementation, a processor determines data usage effectiveness information related to an entity's workflow based on workflow data collected related to the entity's operations and metrics determined based on the data. For example, the processor may base the determination on target workflow information and priority information associated with the target workflow information compared to the entity workflow information.

The processor may output information related to the determined data usage effectiveness. The information about the determined data usage effectiveness may be used by the processor, for example, to compare or improve the degree to which the entity collects and uses data. The automatically determined data usage effectiveness information may be used to recommend changes to the way an organization collects or uses workflow data. For example, the processor may recommend changes to equipment settings and/or additional types of data to collect. The information may be used to compare an entity to another entity, such as for a client to determine which entity to work or partner with. The information may be used by the processor to determine a degree of compatibility between entities related to a level or type of data usage effectiveness, and the compatibility information may be used, for examples, to facilitate entities partnering together.

Figure 1:
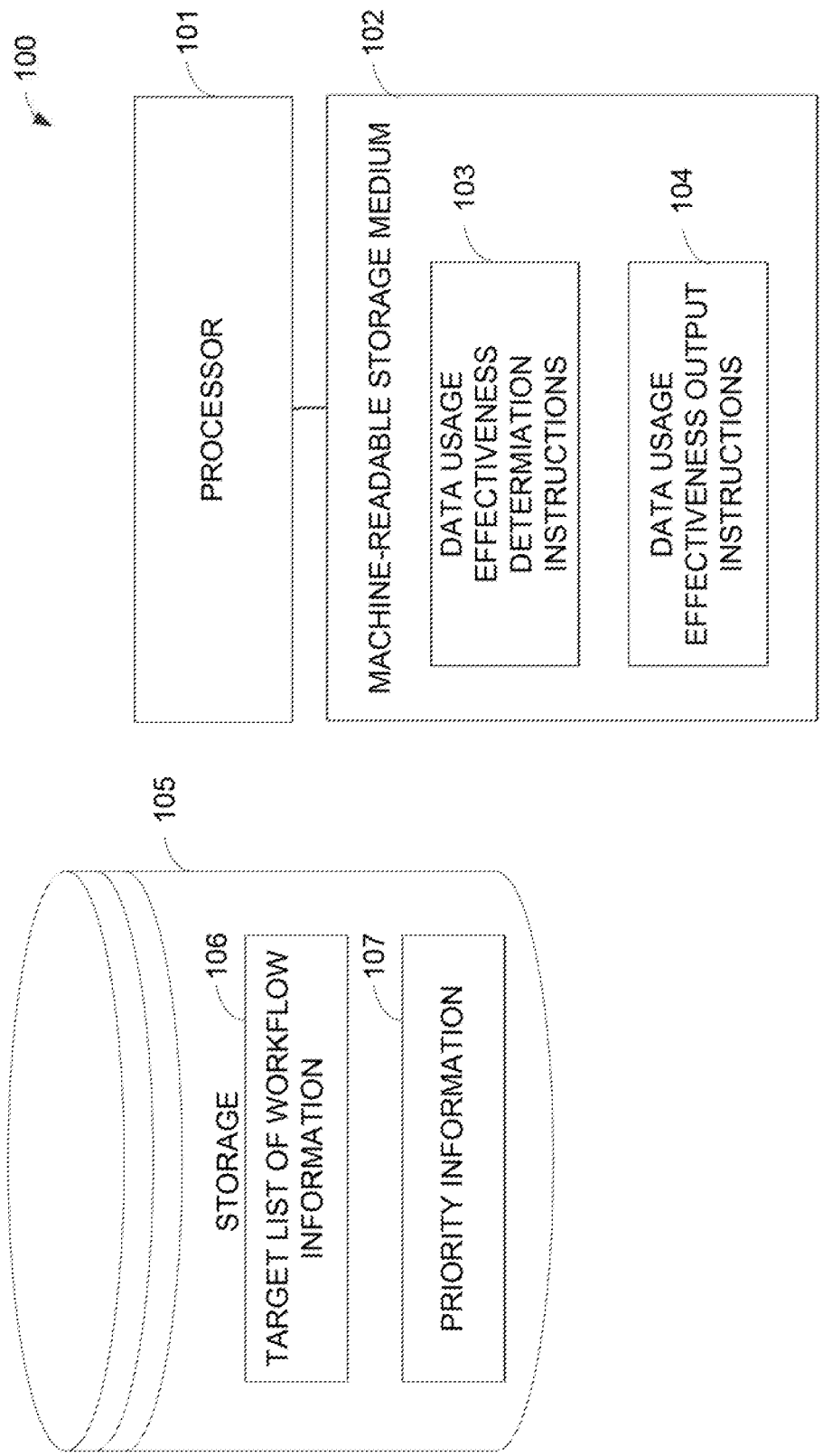
FIG. 1 is block diagram illustrating one example of a computing system to determine data usage effectiveness.

FIG. 1 is a block diagram illustrating one example of a computing system 100 to determine data usage effectiveness. For example, the computing system 100 may access information related to collected data and determined metrics related to the entity workflow operations, and the computing system 100 may determine information about the data usage effectiveness of the entity based on the accessed information. The computing system may determine the data usage effectiveness related to, for example, the entity as a whole, a particular process performed by the entity, or a particular set of equipment used by the entity. The computing system 100 includes a processor 101, a machine-readable storage medium 102, and a storage 105.

The storage 105 may be any suitable storage device for communicating with the processor 101. The storage 105 may include target list of workflow information 106 and priority information 107. The processor 101 may determine and store the target list of workflow information 106 and priority information 107.

The target list of workflow information 106 may include any suitable information related to workflow information. The target list of workflow information 106 may include information about collected data and metrics created based on the collected data. The target list of workflow information 106 may be in any suitable format. For example, the target list of workflow information 106 may be a list of data and/or metrics. In one implementation, the target list of workflow information 106 includes additional information about the workflow information, such as relationships between pieces of information and/or associations between the information and tasks, sites, or equipment. The target list of workflow information 106 may be related to, for example, job shifts, workflow process, demand, system wide metrics, or supplies. As an example, the target list of workflow information 106 may include beginning of worker break, queue size when a task comes to a machine and leaves a machine, service time to complete a task, release task time, machine up time, task failed, task exits, task entering queue, order of admission, and change in equipment supply.

The priority information 107 may be any suitable priority information related to relative priority information of the pieces of information in the target list of workflow information 106. The priority information 107 may indicate the importance of a piece of data or particular metric to an overall data usage effectiveness. The priority information 107 may be associated with a category of information or with a particular piece of information. In one implementation, the priority information 107 is related to the relationship of the piece of workflow information to other pieces of information and the importance of the pieces of information to which it is related to. For example, the priority of a piece of workflow information may be related to the number or metrics it is associated with, the effect on an association metric, and/or a priority of an associated metric.

The processor 101 may be a central processing unit (CPU), a semiconductor-based microprocessor, or any other device suitable for retrieval and execution of instructions. As an alternative or in addition to fetching, decoding, and executing instructions, the processor 101 may include one or more integrated circuits (ICs) or other electronic circuits that comprise a plurality of electronic components for performing the functionality described below. The functionality described below may be performed by multiple processors.

The processor 101 may communicate with the machine-readable storage medium 102. The machine-readable storage medium 102 may be any suitable machine readable medium, such as an electronic, magnetic, optical, or other physical storage device that stores executable instructions or other data (e.g., a hard disk drive, random access memory, flash memory, etc.). The machine-readable storage medium 102 may be, for example, a computer readable non-transitory medium. The machine-readable storage medium 102 may include data usage effectiveness determination instructions 103 and data usage effectiveness output instructions 104.

The data usage effectiveness determination instructions 103 may include instructions to determine data usage effectiveness of an entity based on entity workflow information, such as workflow data collected and workflow metrics determined based on the entity workflow information compared to the target workflow information 106 and the priority information 107. The processor may determine a subset of data from the target list of workflow information 106 that may applicable to the particular entity, such as based on a set of criteria related to the information in the target list of workflow list of information 106.

The processor 101 may determine which data in the target list of workflow information 106 is similar to the workflow information collected for the entity, and which workflow information is missing from the entity workflow information but included in the target list of workflow information 106. The data usage effectiveness may be determined on which workflow information is missing as well as the priority information associated with the missing workflow information.

The data usage effectiveness may be, for example, a score, level, ranking, or other information indicating the data usage effectiveness. The data usage effectiveness may indicate a degree to which the entity uses data related to its workflow compared to the degree to which the entity would be capable of using the workflow information.

The data usage effectiveness output instructions 104 includes instructions to output information related to the determined data usage effectiveness. For example, the processor may display, transmit, or store information related to the data usage effectiveness. The processor may determine recommendations for the entity based on the output. For example, the processor may analyze the missing entity workflow information to determine if there is a particular type of data that the entity should collect, such as data from a particular type of equipment. The processor may compare the output to equipment settings and recommend or automatically change equipment settings in response to the output. For example, there may be equipment settings related to which data is collected or stored. The processor 101 may cause a user interface to be displayed to provide information to a machine operator as to how to change equipment settings. The processor 101 may determine partners to recommend to the entity based on the output, such as partners to assist in creating a more data driven organization.

Figure 2:
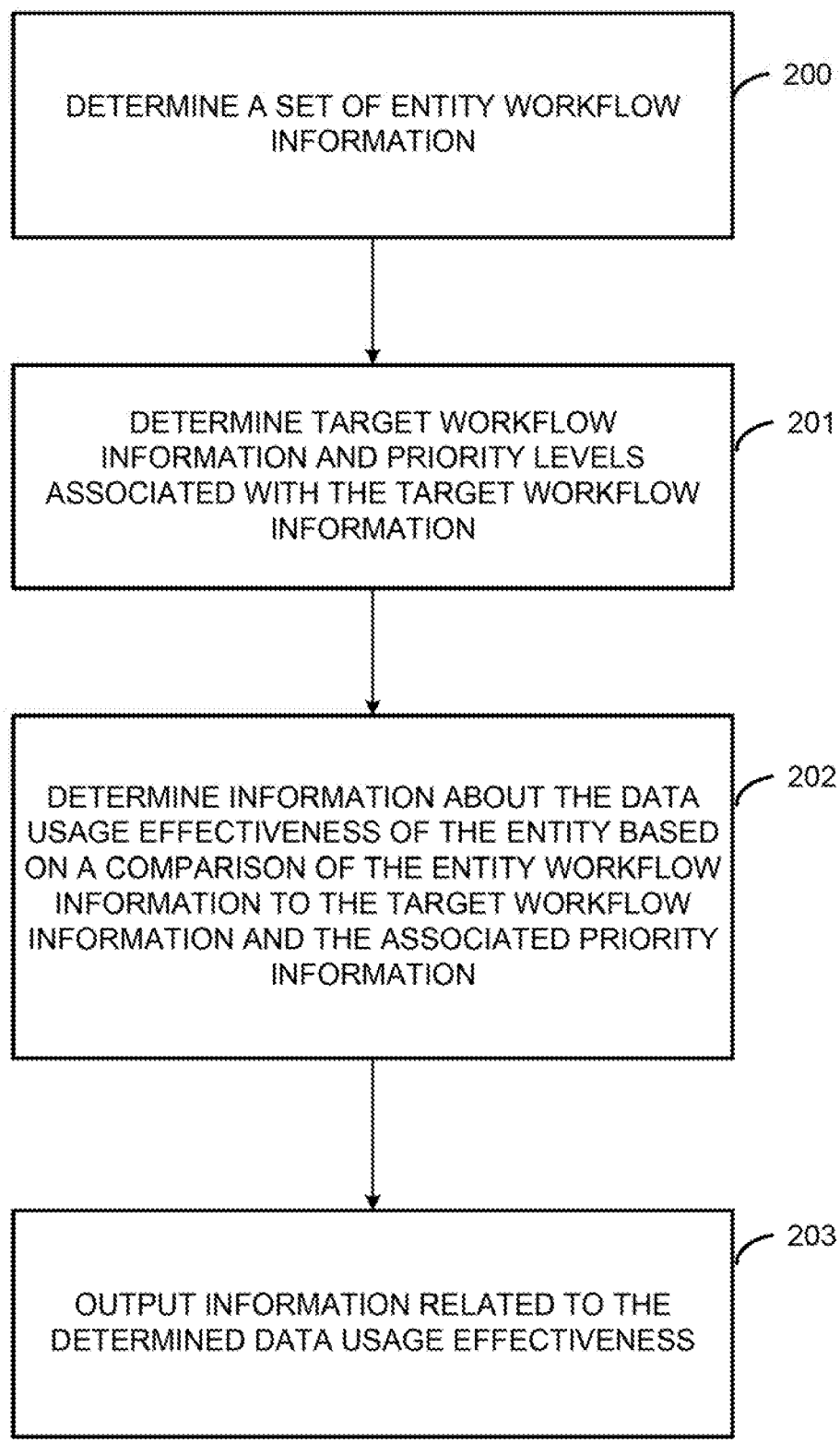
FIG. 2 is a flow chart illustrating one example of a method to determine data usage effectiveness.

FIG. 2 is a flow chart illustrating one example of a method to determine data usage effectiveness. For example, a processor may determine the data usage effectiveness of an entity based on a comparison of the data usage information related to the entity to target data usage information. The data usage effectiveness may indicate the degree to which the entity uses workflow data to its capacity. Greater data usage effectiveness may indicate a more data driven entity. The method may be implemented, for example, by the processor 101 of FIG. 1.

Beginning at 200, a processor determines a set of entity workflow information. The entity may be any suitable entity, such as a company or other organization. The entity may be a portion of a larger entity, such as a site within an organization. The workflow data may be any suitable data related to a process associated with the entity, such as a healthcare, manufacturing, additive manufacturing, or transportation process. The processor may determine the set of entity workflow data collected in any suitable manner. For example, the processor may receive log information, such as production log information, that includes information about data variables and values.

The entity workflow information may include workflow data collected and/or metrics determined based on the collected workflow data. The processor may determine the set of determined metrics in any suitable manner. For example, the processor may determine the metrics based on the same log or based on additional information about information calculated based on the underlying data. In one implementation, the processor associates the metrics and data, such as based on which data a particular metric is determined based on. In one implementation, the processor determines that a particular piece of data is collected based on presence of the information in a metric. The processor may determine the information from multiple sources, such as a separate production log created by each piece of equipment. The processor may aggregate the workflow information and/or associate the workflow information with particular pieces of equipment or types of process. For example, a different type of print job on the same piece of equipment may be associated with a different set of collected workflow data. The entity workflow information may be associated with a time horizon, such as where different types of workflow information are collected for different time periods. The entity may aggregate workflow information to determine applicable metrics over particular time frames, such as the number of jobs per day, and the aggregate workflow information associated with the time horizon may be included within the entity workflow information.

Figure 3A:
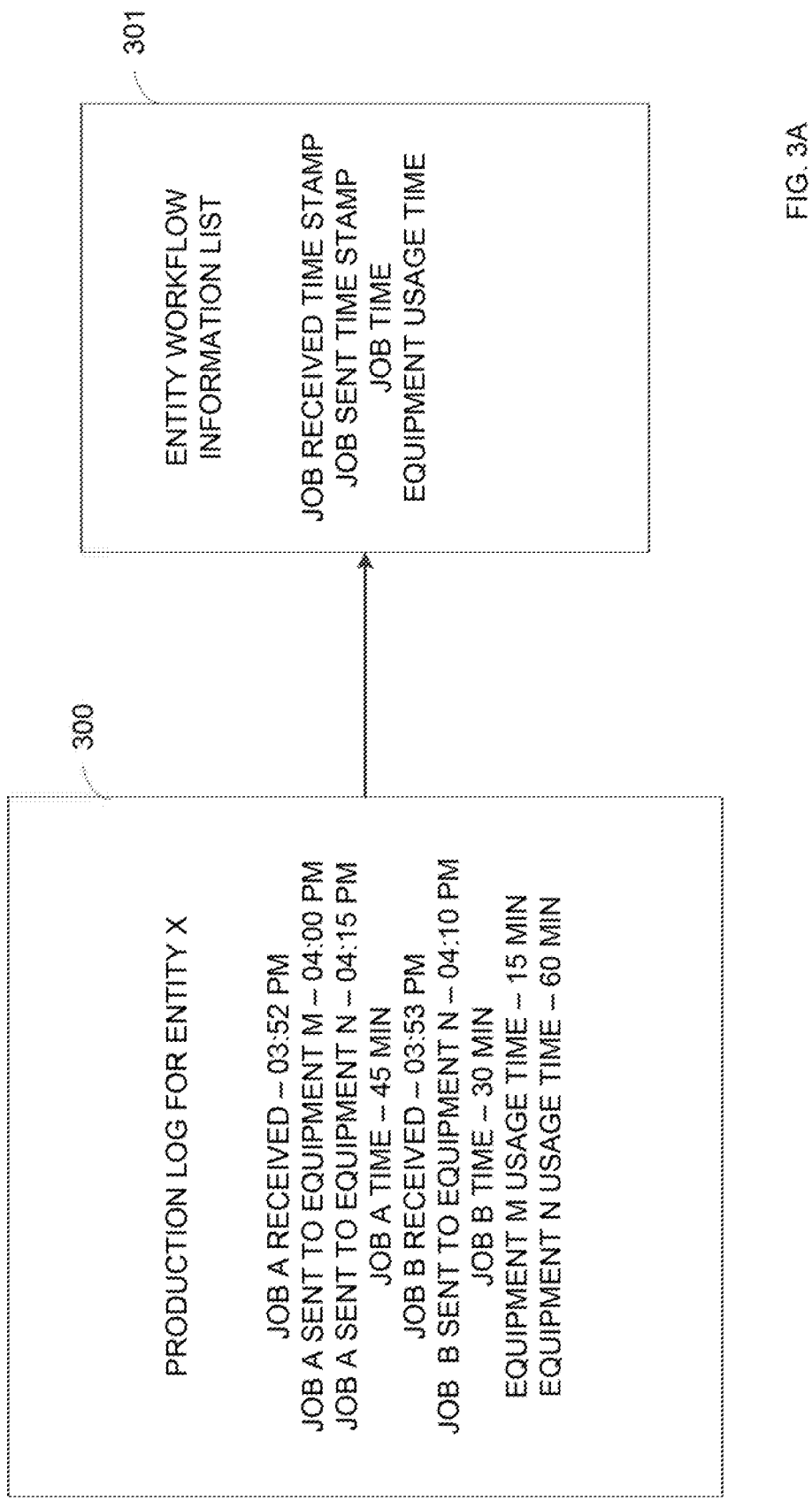

FIGS. 3A-3D are diagrams illustrating examples of determining data usage effectiveness. FIG. 3A is a diagram illustrating one example of determining workflow information captured and determined by an Entity X. For example, a processor may analyze a production log associated with Entity X to determine the unique types of events included within the production log. Block 300 shows a production log for Entity X. The processor may determine that the workflow information shown in block 301 is used by Entity X based on the information in the production log 300. For example, Entity X uses workflow information related to a job received time stamp, job sent time stamp, job time, and equipment usage time.

Referring back to FIG. 2 and continuing to 201, a processor determines target workflow information and priority information associated with the target workflow information. The processor may determine the workflow information in any suitable manner. For example, the processor may determine the target workflow information components based on the type of entity or type of workflow associated with the entity. For example, different workflow information components may be selected based on the size of the entity and/or type work experienced by the entity, such as the type of common orders for the entity in a manufacturing environment. The processor may select an entity and use workflow information related to a second entity to create a target list of workflow information. The second entity may be selected based on similarity to the first entity and/or based on the level of data usage effectiveness associated with the second entity. The processor may aggregate entity workflow information from multiple entities to create the target list of information. For example, the processor may determine the unique workflow information captured and determined by a set of entities and select the target workflow information from the unique workflow information.

The processor may determine the target list based on the output of a simulation. For example, the processor may run a simulation with factors similar to the particular entity, such as similar demand. The processor may analyze a production log associated with the simulation or an output list of metrics and data from the simulation. In one implementation, the processor recommends particular types of jobs or particular jobs to the simulator to generate compatible output to the entity. In one implementation, the processor recommends a test job to the entity to compare to the simulation output and/or recommends a test job to the simulator that matches an order or workflow item associated with the entity.

Figure 3B:
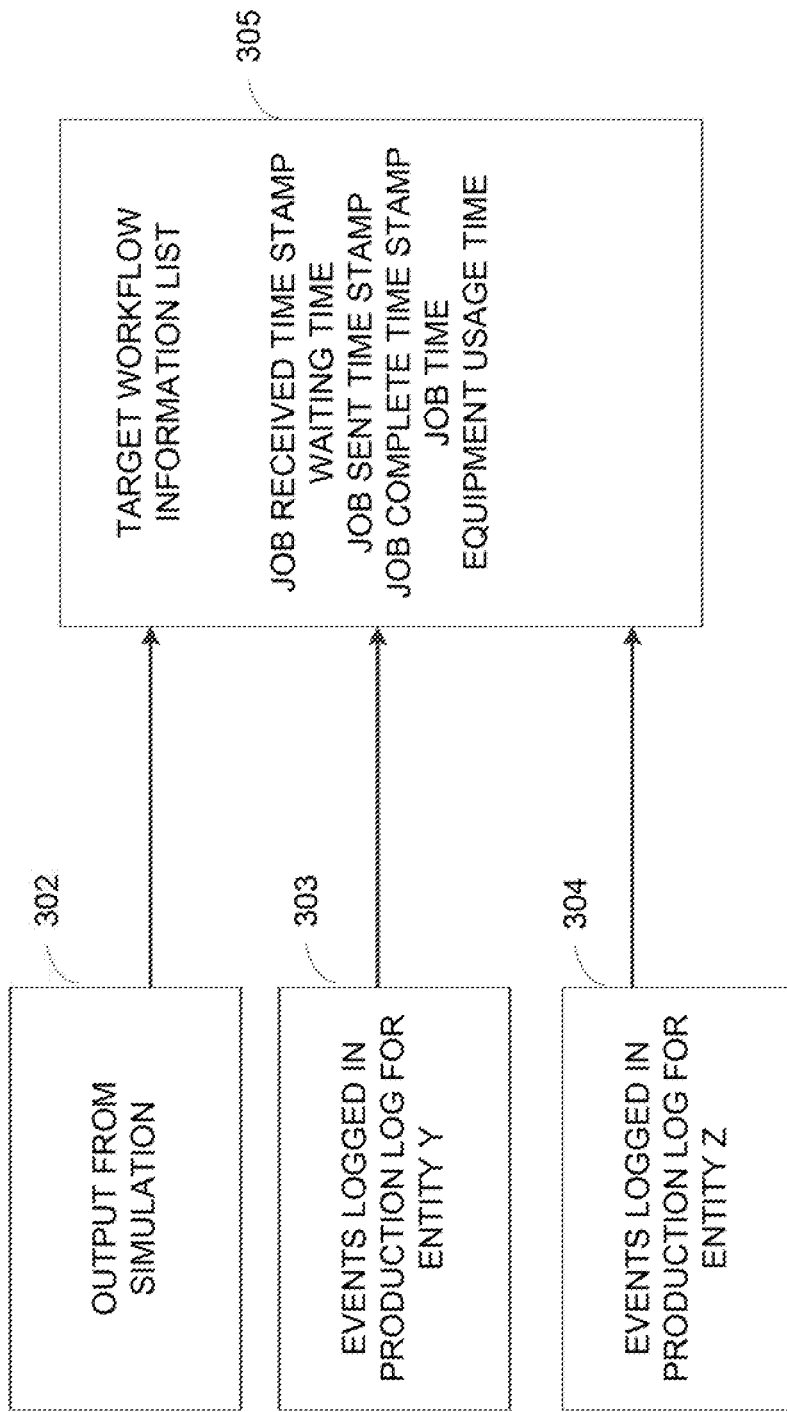

FIG. 3B is a diagram illustrating one example of determining target workflow information components. A processor analyzes input information from block 302 related to output from a simulation, block 303 related to events logged in a production log for entity Y, and block 304 related to events logged in a production log for entity Z. The processor may use information from a single source based on the particular entity being analyzed or may use information from multiple sources, such as where the sources are weighted based on relevance to the particular entity. Block 305 shows the target workflow information list including job received time stamp, waiting time, job sent time stamp, job complete time stamp, job time, and equipment usage time.

The processor may determine the priority information in any suitable manner. The processor may determine the priority information based on which entity is associated with the workflow information, such as whether the entity more closely resembles the entity being evaluated, whether an entity that is associated with a greater degree of data usage effectiveness includes the pieces of workflow information, and/or whether more entities collected or determined the particular piece of information.

The processor may determine the priority information based on a relationship between the collected data and determined metrics. In one implementation, the processor creates a tree structure with nodes representing collected data and determined metrics such that the nodes are connected to represent a relationship between the nodes. The processor may determine the priority based on the height of the tree such that data that there is higher priority associated with data or metrics at higher levels that feed into a greater number of workflow metrics.

Referring back to FIG. 2 and continuing to 202, a processor determines information about the data usage effectiveness of the entity based on a comparison of the entity workflow information to the target workflow information and the associated priority information. The processor may determine information about the data usage effectiveness in any suitable manner. For example, the processor may determine priority information associated with the target workflow information and compare the target workflow information to the entity workflow information and weight the comparison based on the priority.

In one implementation, the processor receives a template for mapping a piece of target workflow information to a piece of entity workflow information. The processor may receive user input, such as where the processor causes a user interface to be displayed that shows existing mappings to allow a user to accept or update. The user interface may show areas where the mappings do not exist, indicating a potentially missing metric to allow the user to confirm or manually perform the mapping.

The processor may create a representation of the entity workflow information to compare to the target workflow information, such as where the representation indicates the priority level associated with pieces of information in the target workflow information.

The processor may compare the target workflow information to the entity workflow information in any suitable manner. The processor may compare a representation of the entity workflow information to the target workflow representation, such as where the representations are tree structures with the height indicating the priority level. The missing nodes may be evaluated for each job or item in the workflow or for each unique tree, such as where the types of workflow information generated depend on the particular workflow process. For example, the processor may determine data usage effectiveness as the following where N represents the number of jobs or items that pass through the workflow process:

$$1 - \left( \frac{\left( \prod_1^N \text{proportion of missing nodes}(i) * (\text{height} - \text{level of node}(i)) \right)}{\text{Total number nodes} * \text{height}} \right)$$

Figure 3C:
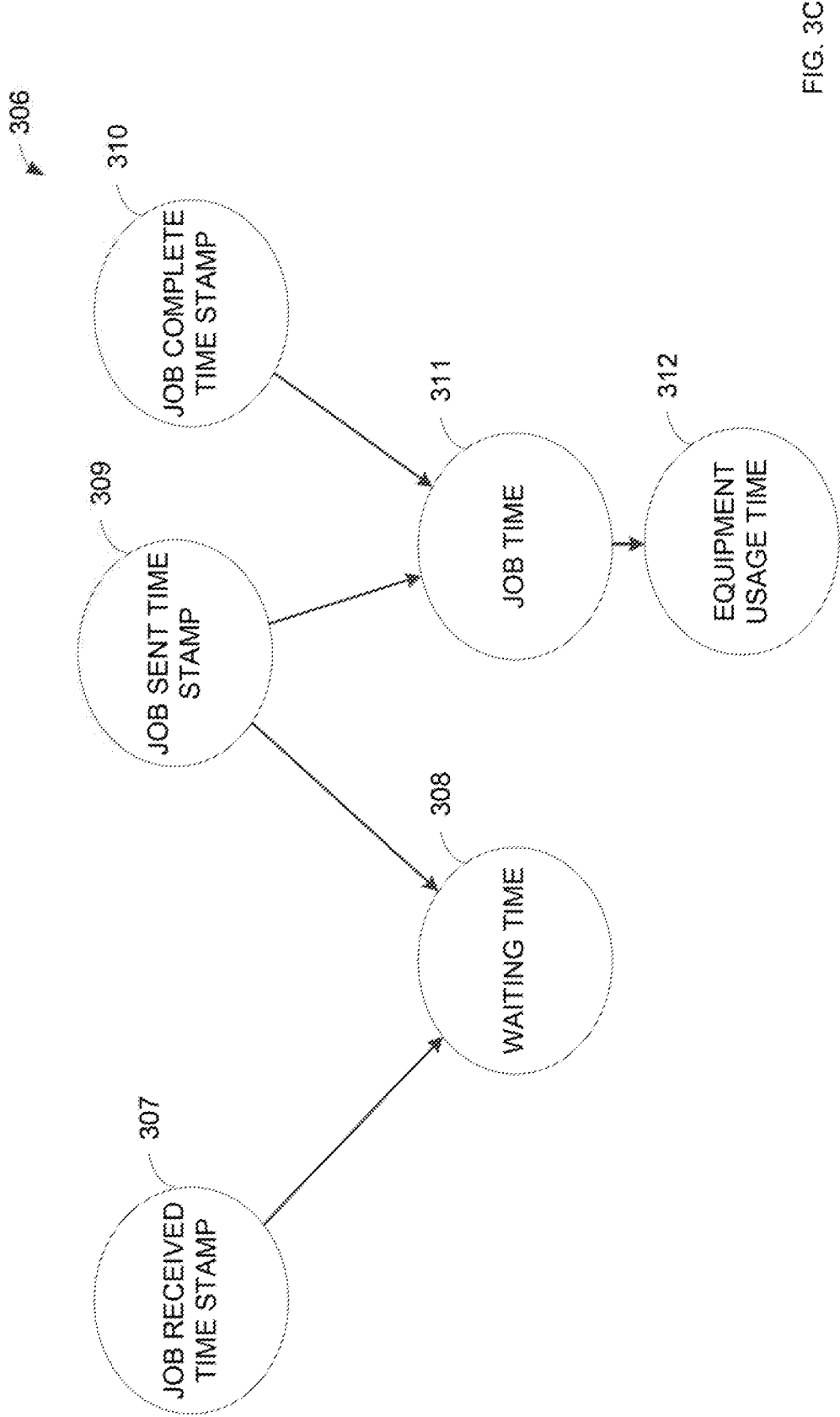

FIG. 3C is a diagram illustrating one example of a representation of the target list of workflow information used to determine data usage effectiveness. The representation 306 includes nodes 307-312 representative of data and metrics from the target list of workflow information 305 from FIG. 3B. The representation 306 includes the nodes in a hierarchy such that a piece of data or metric that is dependent on another node is lower in the hierarchy than that node and connected to that node. For example, node 308 for waiting time is representative of a metric determined based on both nodes 307 and 309.

FIG. 3D is a diagram illustrating one example of a representation 313 of the entity list of workflow information 301 from FIG. 3A. The representation 313 may be used to show dependencies between information in the entity list of workflow information 301. The dependencies may be used, for example, to map differing named items to similar concepts and/or to determine the priority level of the concepts.

A processor may compare the representation 306 to the representation 313 to determine the data usage effectiveness of Entity X. For example, the representation 313 includes the information from nodes 307, 309, 311, and 312 from the target workflow information representation 306, and the representation 313 does not include the information from nodes 308 and 310. The processor may perform post processing on the representation 313 to add nodes related to information that is not explicitly included within the entity workflow information list 301. For example, the representation 313 does not include job complete time stamp node 310. However, the representation 313 includes job time node 316 and job set time stamp node 315. The processor may determine that the information from job complete time stamp node 310 is used by Entity X despite not being specifically listed in the entity workflow information list 301. The processor may determine the data usage effectiveness based on the representation 313 missing node 308 and based on a priority level associated with the missing node 308 based on its location at the $2^{nd}$ level in the hierarchy.

Continuing to 203, a processor outputs information related to the determined data usage effectiveness. The processor may output the information in any suitable manner, such as by transmitting, storing, or displaying the information. The processor may transmit the information to another device for analysis. The processor may transmit information about the data usage effectiveness to a device associated with the entity. The processor may store information about the data usage effectiveness, such as where the processor stores information about the data usage effectiveness of multiple entities. The processor may cause a user interface to be displayed to provide information about the data usage effectiveness. The user interface may provide information about the overall data usage effectiveness and/or information about areas where the entity did not use data effectively, such as where an area of low data usage effectiveness occurs for a type of event and/or for a particular worker group, supply type, or equipment type. For example, information about missing nodes from a representation, such as representation 313 in FIG. 3D, may be provided. In one implementation, the user interface provides summary information about the areas to improve, such as information about the type of information not being collected or particular equipment where the data usage effectiveness is lower.

The processor may determine a recommendation for the entity based on the data usage effectiveness information. For example, the processor may determine a piece of equipment associated with low data usage effectiveness. The processor may receive information about current settings associated with the piece of equipment and determine setting changes to increase the data usage effectiveness of the piece of equipment. For example, the target workflow information list may include information about settings associated with each piece of workflow information, and the processor may output information about the settings associated with the missing piece of information.

The processor may recommend partners for the entity based on the data usage effectiveness. For example, the processor may recommend a different partner depending on the level and/or a particular data deficiency type associated with the data usage effectiveness. In one implementation, the processor provides information about other entities having higher overall data usage effectiveness and/or higher data usage effectiveness in an area of lower data usage effectiveness for the particular entity.

The processor may determine data usage effectiveness information for multiple entities and rank the entities based on relative data usage effectiveness. For example, a potential customer may view the relative rankings or search for an entity with a ranking above a threshold.

The processor may group entities based on data usage effectiveness. For example, the processor may determine entities that are compatible based on the data usage effectiveness and/or the data usage effectiveness levels in the same areas, such as related to the same types of processes. Automatically determining data usage effectiveness of an entity may facilitate an entity in becoming more data driven.

The invention claimed is:

1. A computing system, comprising:
a storage to store:
   a list of target workflow information; and
   priority information associated with the target workflow information; and
a processor to:
   compare a set of entity workflow information to the target workflow information and the priority information associated with the target workflow information to determine data usage effectiveness associated with an entity, wherein the entity workflow information comprises at least one of workflow data collected and metrics determined based on the workflow data;
   output information related to the data usage effectiveness that is determined, wherein the data usage effectiveness identifies which information from the target workflow information is missing from the set of entity workflow information;
   determine a type of data of the information that is missing and a piece of equipment that is to collect the information that is missing from the set of entity workflow information;
   compare the data usage effectiveness that is output to settings of the piece of equipment; and
   change the settings of the piece of equipment to collect the type of data of the information that is missing from the set of entity workflow information based on the data usage effectiveness that is output that is compared to the settings of the piece of equipment.

2. The computing system of claim 1, wherein the processor is further to determine a recommendation to improve the data usage effectiveness of the entity.

3. The computing system of claim 1, wherein the processor is further to determine relative data usage effectiveness between the entity and a second entity based on the information that is output.

4. The computing system of claim 1, wherein the processor is further to determine the list of target workflow information based on at least one of:
   workflow information associated with a second entity and
   workflow information associated with a simulation.

5. The computing system of claim 1, wherein the processor is further to determine a priority associated with a piece of information in the list of target workflow information based on at least one of: a number or metrics that the piece of information is associated with, the effect on an associated metric, and a priority of an associated metric.

6. The computing system of claim 1, wherein the processor is further to preprocess the entity workflow information to add entity workflow information determined based on the entity workflow information.

7. A method, comprising:
   determining a set of entity workflow information, wherein the entity workflow information comprises at least one of workflow data collected and metrics determined based on the workflow data that is collected;
   determining target workflow information and priority levels associated with the target workflow information;
   determining information about data usage effectiveness of an entity based on a comparison of the set of entity workflow information to the target workflow information and the priority levels associated with the target workflow information, wherein the data usage effectiveness identifies which information from the target workflow information is missing from the set of entity workflow information;
   outputting information related to the data usage effectiveness that is determined;
   determining a type of data of the information that is missing and a piece of equipment that is to collect the information that is missing from the set of entity workflow information;
   comparing the data usage effectiveness that is output to settings of the piece of equipment; and
   changing the settings of the piece of equipment to collect the type of data of the information that is missing from the set of entity workflow information based on the comparing.

8. The method of claim 7, further comprising determining priority information associated with data in a list of the target workflow information based on at least one of: a number of metrics to which the data contributed and priority information associated with metrics to which the data contributed.

9. The method of claim 7, wherein determining the target workflow information comprises:
    determining demand associated with the set of entity workflow information;
    running a simulation based on the demand that is determined; and
    determining the target workflow information based on the simulation.

10. The method of claim 7, further comprising selecting an action to improve the data usage effectiveness based on the information that is output.

11. The method of claim 7, wherein determining the data usage effectiveness comprises:
    creating a target tree with nodes representing the target workflow information, wherein tree edges represent relationships between the target workflow information and wherein a height of the target tree indicates a priority associated with a node; and
    comparing the target tree with an entity tree representative of the set of entity workflow information.

12. The method of claim 11, wherein determining the data usage effectiveness comprises determining a data usage effectiveness score based on at least one of: a proportion of missing tree nodes in the entity tree compared to the target tree, the number of tree nodes in the target tree, and the height of the tree nodes in the target tree.

13. A machine-readable non-transitory storage medium comprising instructions executable by a processor to:
    determine data usage effectiveness information related to a workflow of an entity based on workflow data collected related to operations and metrics of the entity determined based on the data usage effectiveness information, wherein the data usage effectiveness is determined based on a comparison of the workflow of the entity to target workflow information and priority information associated with the target workflow information, wherein the data usage effectiveness identifies which information from the target workflow information is missing from the workflow of the entity;
    output information related to the data usage effectiveness that is determined;
    determine a type of data of the information that is missing and a piece of equipment that is to collect the information that is missing from the workflow information of the entity;
    compare the data usage effectiveness that is output to settings of the piece of equipment; and
    change the settings of the piece of equipment to collect the type of data of the information that is missing from the set of entity workflow information based on the data usage effectiveness that is output that is compared to the settings of the piece of equipment.

14. The machine-readable non-transitory storage medium of claim 13, further comprising instructions to:
    create a representation including nodes representative of at least one of the workflow data and metrics, wherein the nodes are connected based on a relationship between information associated with the nodes; and
    cause a user interface to be displayed including information related to the representation that is created.

15. The machine-readable non-transitory storage medium of claim 13, wherein the workflow is associated with at least one of manufacturing, additive manufacturing, healthcare, and transportation.

* * * * *